(12) United States Patent
Bomse et al.

(10) Patent No.: US 6,351,309 B1
(45) Date of Patent: *Feb. 26, 2002

(54) DUAL MODULATION LASER LINE-LOCKING TECHNIQUE FOR WAVELENGTH MODULATION SPECTROSCOPY

(75) Inventors: David S. Bomse; D. Christian Hovde; Joel A. Silver, all of Santa Fe, NM (US)

(73) Assignee: Southwest Sciences Incorporated, Santa Fe, NM (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/347,814

(22) Filed: Nov. 30, 1994

Related U.S. Application Data

(63) Continuation of application No. 07/911,947, filed on Jul. 10, 1992, now abandoned, which is a continuation-in-part of application No. 07/740,798, filed on Aug. 6, 1991, now abandoned.

(51) Int. Cl.[7] .......................... G01N 21/35; G01N 21/61
(52) U.S. Cl. ........................ 356/437; 250/343
(58) Field of Search ................. 356/325–326, 356/300, 437, 409, 319; 372/32; 250/343

(56) References Cited

U.S. PATENT DOCUMENTS

| | | |
|---|---|---|
| 3,395,365 A | 7/1968 | Fork |
| 3,471,803 A | 10/1969 | Forster |
| 3,593,189 A | 7/1971 | Buhrer |
| 3,609,583 A | 9/1971 | Brun |
| 3,742,382 A | 6/1973 | Smith |
| 3,967,211 A | 6/1976 | Itzkan et al. |
| 4,297,035 A | 10/1981 | Bjorklund ............... 356/402 |
| 4,410,273 A | * 10/1983 | Mantz et al. ............ 356/319 |
| 4,434,490 A | 2/1984 | Kavaya et al. |
| 4,594,511 A | 6/1986 | Cooper et al. |
| 4,765,736 A | 8/1988 | Gallagher et al. ......... 356/300 |
| 4,817,100 A | 3/1989 | Cameron et al. |
| 4,856,009 A | 8/1989 | Hall et al. |
| 4,932,775 A | 6/1990 | Wissman et al. |
| 4,937,448 A | 6/1990 | Mantz et al. ............ 250/343 |
| 5,267,019 A | 11/1993 | Whittaker et al. ......... 356/437 |

FOREIGN PATENT DOCUMENTS

DE          3734401          4/1989

OTHER PUBLICATIONS

"Double frequency modulation spectroscopy: high modulation frequency with low–bandwidth detectors," by D.E. Cooper et al., Applied Optics, vol. 24, No. 9, pp. 1327–1332 (May 1, 1985).

"Modulation Broadening of NMR and ESR Line Shapes," by G.V.H. Wilson, J. Appl. Phys., vol. 34, pp. 3276–3285 (1963).

"Analytical Line Shapes for Lorentzian Signals Broadened by Modulation," by R. Arndt, J. Appl. Phys., vol. 36, pp. 2522–2524 (1965).

"Frequency Stabilization of Gas Lasers," by A. White, IEEE Journal of Quantum Electronics, vol. QE–1, No. 8., pp. 349–357 (1965).

(List continued on next page.)

*Primary Examiner*—F. L. Evans
(74) *Attorney, Agent, or Firm*—Jeffrey D. Myers; Deborah A. Peacock

(57) ABSTRACT

Disclosed are a method and apparatus for dual modulation of an optical spectroscopy laser. Demodulation is accomplished in a manner resulting in measurement of absorbance of a gas species, as well as stabilization of laser wavelength and baseline noise reduction.

40 Claims, 8 Drawing Sheets

OTHER PUBLICATIONS

"400 Hz frequency stability of a GaAIAs laser frequency locked to the Rb (D2) line," by T. Shay et al. Optical Engineering, vol. 29, No. 6, pp. 681–683 (1990).

"Harmonic Detection with Tunable Diode Lasers–Two Tone Modulation," by D. Cassidy et al., Appl. Phy. B, vol. 29, pp. 279–285 (1982).

Bomse, D.S., "Dual–Modulation laser Line–Locking Scheme," *Applied Optics*, vol. 30, p 2922 (Jul. 20, 1991).

Sun and Whittaker, "Novel Etalon Fringe Rejection Technique for Laser Absorption Spectroscopy," *Applied Optics*, vol. 31, No. 24, pp 4998–5002, Aug. 20, 1992.

Sun and Whittaker, et al., "Combined Wavelength and Frequency Modulation Spectroscopy: A Novel Diagnostic Tool for Materials Processing," *Applied Optics*, vol. 32, No. 6, pp 885–893 Feb. 20, 1993.

Sun and Whittaker, "Dynamic Resonant Peak Locking Scheme for Diode Laser Modulation Spectroscopy," *Optical Engineering*, vol. 32, No. 3, pp 453–457 3/93.

* cited by examiner

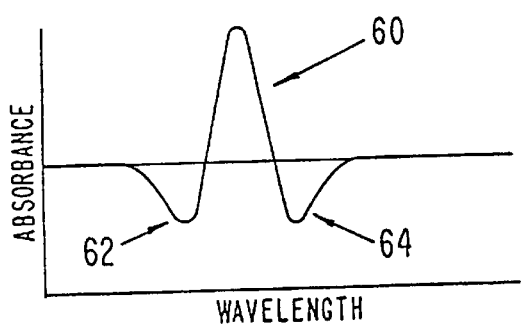
FIG—3a
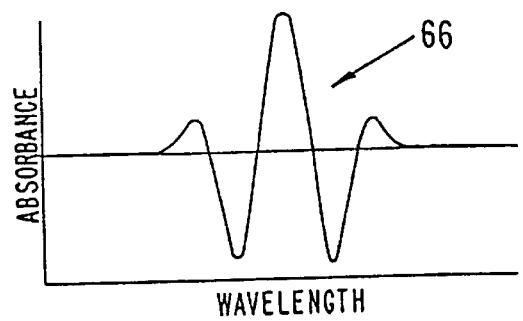
FIG—3b
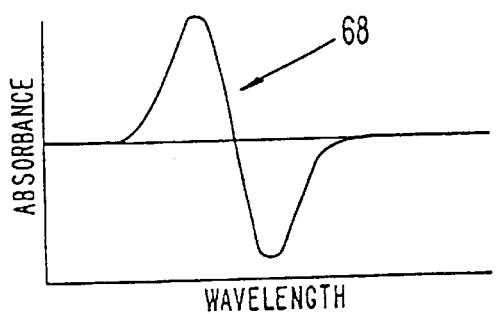
FIG—3c
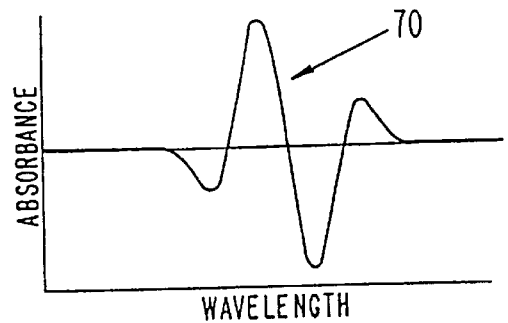
FIG—3d

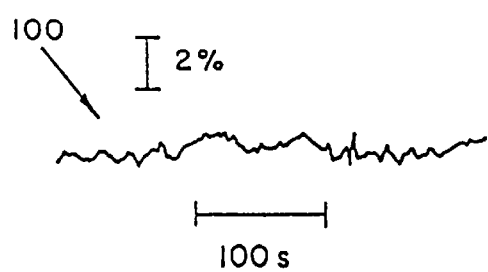
FIG—5a
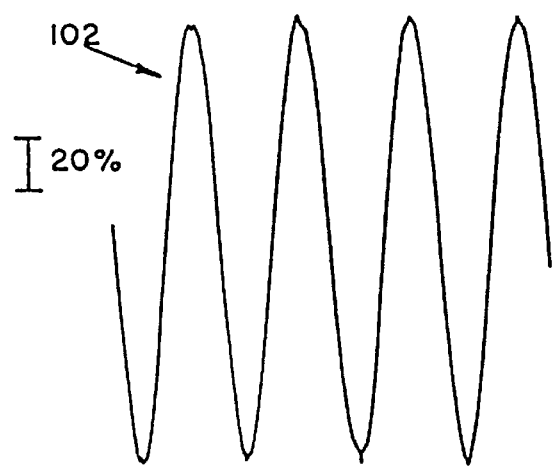
FIG—5b
FIG—5c
FIG—5d

DUAL MODULATION LASER LINE-LOCKING TECHNIQUE FOR WAVELENGTH MODULATION SPECTROSCOPY

CROSS-REFERENCE TO RELATED APPLICATIONS

This is a continuation of application Ser. No. 07/911,947 filed on Jul. 10, 1992, now abandoned, which is a continuation-in-part application of U.S. patent application Ser. No. 07/740,798, entitled Dual Modulation Laser Line-Locking For Wavelength Modulation Spectroscopy, to David S. Bomse, filed on Aug. 6, 1991, now abandoned, the teachings of which are incorporated herein by reference.

GOVERNMENT RIGHTS

This invention was made with U.S. Government support under Contract DE-FG03-90ER81053 awarded by the Department of Energy. The Government has certain rights in this invention.

BACKGROUND OF THE INVENTION

1. Field of the Invention (Technical Field)

The invention has application to instruments that use optical spectroscopy with variable-wavelength light sources to monitor a known species.

2. Background Art

Optical spectroscopy is a well-established technique that allows quantitation of a known species within a sample by measuring the fraction of light intensity that is absorbed by the sample at a specific wavelength. The underlying scientific principle, known as Beer's Law, is expressed as:

$$I/I_0 = e^{-n\sigma l}, \qquad (1)$$

where I is the light intensity after passing through the sample, $I_0$ is the initial light intensity, n is the species number density or concentration, $\sigma$ is the species optical absorption cross-section which is a fundamental property of the species and depends on wavelength, and l is the optical path length through the sample. Typically, $\sigma$ and l are well known, implying that measurement of absorbance, where absorbance is defined as $\alpha = -\log_e (I/I_0)$, is sufficient to determine n, the species number density within the sample.

Continuous monitoring of a target species concentration can be made practical through the use of continuous measurement of optical absorbance. It is instructive to focus on applications in which the light source is a wavelength tunable continuous-wave laser and the sample probed contains a gas exhibiting an absorption spectrum composed of well resolved, narrow lines. At least one of the absorption lines of the target gas is assumed to lie within the accessible wavelength tuning range of the laser. The quantity of the gas in a sample is determined by measuring the absorbance of the laser light when the laser wavelength is made coincident with one pre-selected absorption feature.

Monitoring species at low concentrations requires measuring accurately weak absorbances, i.e., $\alpha < 10^{-3}$. Signals due to weak absorbances are often obscured by laser noise. The dominant noise source is known as "1/f" noise because it decreases with increasing frequency; therefore, most strategies for improving the signal-to-noise ratio of absorbance measurements attempt to shift the detection bandwidth to high frequencies. One such approach, wavelength modulation spectroscopy, is effective for avoiding laser 1/f noise. The technique is described by Wilson (G. V. H. Wilson, "Modulation Broadening of NMR and ESR Line Shapes," *J. Appl. Phys.* 34, 3276–3285 (1963)) and by Arndt (R. Arndt, "Analytical Line Shapes for Lorentzian Signals Broadened by Modulation," *J. Appl. Phys.* 36, 2522–2524 (1965)). The laser wavelength is modulated at a frequency $\Omega$ with the modulation amplitude chosen such that the wavelength excursions are comparable to the width of the absorption line being investigated. The laser beam passes through the sample and impinges on a detector that provides a voltage or a current that is linearly proportional to the laser light power or intensity. The detector output is demodulated at the modulation frequency, or some integral multiple of the modulation frequency, to produce a signal that can be related to the sample absorbance. Demodulation methods are usually identified as 1f, 2f, 4f, etc., for demodulation at frequencies $\Omega$, $2\Omega$, $4\Omega$, respectively. Demodulation using an odd harmonic, that is, 1f, 3f, etc. gives spectral waveforms that are typically zero when the laser wavelength is coincident with the gas absorption line center wavelength and that exhibit inversion symmetry about the line center wavelength. Detection using an even harmonic, that is 2f, 4f, etc., gives signals with extrema when the laser wavelength is at line center and these signal amplitudes are proportional to sample absorbance. FIG. 1 includes a representative absorption line spectrum, 10, as well as 1f, 2f, 3f and 4f spectral waveforms, 12, 14, 16, and 18, respectively.

To make practical the continuous, long term monitoring of the gas, the laser wavelength must be fixed at a wavelength within the absorption line of the gas. It is often preferred that the fixed wavelength coincide with the center of the absorption line. In the absence of active control of the laser wavelength, the laser wavelength will vary due to changes in the laser temperature, the laser gain profile, etc. Diode laser wavelengths can drift by an unacceptably large amount over time periods of less than 10 minutes. A number of schemes exists that use a selected absorption line of the target gas as a wavelength standard for controlling the laser wavelength. These techniques are known as line-locking methods and are well described by White (A. D. White, "Frequency Stabilization of Gas Lasers," *IEEE Journal of Quantum Electronics* QE-1, 349–357 (1965)), with improvements to the art presented by Brun (Henri Brun, "Arrangement for Controlling the Frequency of a Light Source Using an Absorption Cell," U.S. Pat. No. 3,609,583, issued Sep. 28, 1971), by Smith (Peter William Smith, "Apparatus for Stabilizing a Laser to a Gas Absorption Line," U.S. Pat. No. 3,742,382, issued Jun. 26, 1973), by Buhrer (Carl F. Buhrer, "Frequency Stabilization System," U.S. Pat. No. 3,593,189, issued Jul. 13, 1971) and by Kavaya (Michael J. Kavaya and Robert T. Menzies, "Spectrophone Stabilized Laser with Line Center Offset Frequency Control," U.S. Pat. No. 4,434,490, issued Feb. 28, 1984). In each invention, a portion of the laser beam is directed through a reference cell holding a known amount of the gas being studied and then onto a detector. The laser wavelength is modulated by a small amount about its nominal wavelength and this modulation causes synchronous changes in the detector output. The usefulness of the modulation scheme is evident from FIG. 1 which includes a representative absorption line 10, i.e., absorbance plotted against laser wavelength. If wavelength modulation amplitude is comparable to the wavelength width of the absorption line and the detector output is processed using a phase sensitive detector, then the resulting spectral waveform looks like a 1f spectral waveform 12. The signal is zero when the laser average wavelength matches the absorption line center and it varies linearly with small displacements in wavelength about the line center. The signal can be used as a discriminant to correct the laser average wavelength back to the center of the absorption line.

It is the intent of most laser stabilization schemes to obtain the smallest possible fluctuations in the laser wavelength and, in many cases, demonstrated root mean squared wavelength fluctuations are as small as 1 part in $10^{10}$ to $10^{12}$. For example, both Brun and Smith use the method of saturated absorbance to achieve reference line widths considerably smaller than the line widths exhibited by the same reference gas in a conventional absorption measurement. These narrow line widths provide more precise control of the laser wavelength. The magnitude of the wavelength excursions required to implement wavelength modulation spectroscopy are at least as large as the absorber gas Doppler linewidth, which is larger than 1 part in $10^7$ for nearly all gaseous absorbers.

The wavelength stabilization method disclosed by Cook is only applicable to lasers in which the output power as a function of wavelength exhibits the phenomenon known as a "Lamb dip." Cook's invention is applicable only to some gas lasers in which the extent of continuous wavelength tunability is defined by the Doppler profile of an optical transition of a known gaseous component of the laser gain medium. Similarly, Fork's laser stabilization method (R. L. Fork, "Frequency Stabilized Optical Maser," U.S. Pat. No. 3,395,365, issued Jul. 30, 1968) is also limited to lasers making use of an active medium characterized by a Doppler broadened optical emission line.

Kavaya and Mead each disclose methods for stabilizing a laser to an absorption line at a wavelength different from the laser center wavelength. These wavelength offset approaches also use only one modulation frequency and are not useful for absorption measurements of a sample containing an unknown amount of the referenced gas.

Additional art describes laser wavelength stabilization schemes in which the laser has a stabilized output spectrum that is free of modulation. For example, Forster (Donald C. Forster, "Laser Having a Stabilized Output Spectrum," U.S. Pat. No. 3,471,803, issued Oct. 7, 1969) describes a method in which the output wavelength of the laser to be stabilized is compared to the time-varying wavelength of a second laser whose output is modulated. Time-gated measurement of the wavelength difference between the two lasers provides an error signal that is used to control the wavelength of the unmodulated laser. In contrast, the present invention makes it desirable that the laser wavelength be modulated because wavelength modulation is required to measure small absorbances of the sample.

Additional prior art describes wavelength stabilization to an arbitrary wavelength that need not coincide with the wavelength of a specific absorption line of a reference gas. Itzkan (Irving Itzkan and Charles T. Pike, "Laser Wavelength Stabilization," U.S. Pat. No. 3,967,211, issued Jun. 29, 1976) stabilizes the output of a wavelength tunable laser using a Fabry Perot etalon filter. Hall (John L. Hall and Miao Zhu, "Method and Apparatus for Laser Control," U.S. Pat. No. 4,856,009, issued Aug. 8, 1989) modulates the wavelength of the laser light using acousto-optic modulators that are external to the laser. An interferometer, which is similar in design to a Michelson interferometer, provides a phase discriminant that is used to control the laser wavelength. Both Itzkan and Hall describe methods that are less useful than are line locking methods for stabilizing a laser wavelength when the laser will be used for absorbance measurements.

The combination of line locking schemes and wavelength modulation spectroscopy suggests a method for continuous monitoring of a selected species in which line locking maintains the laser average wavelength coincident with the center of an absorption line of the target gas while the absorbance of a sample can be determined using demodulation at an even harmonic of the modulation frequency. Unfortunately, measurement of absorbance as defined by the magnitude of the demodulated sample signal will include fluctuations in the baseline, where the true baseline level is the demodulated detector output measured in the absence of absorbance. The instantaneous absorbance signal deviates from the true value due to the superposition of the baseline fluctuations on the absorbance signal. Fluctuations can be caused by electronic noise, vibration, etc., and the temporal bandwidth of such baseline fluctuations is typically below 1 kHz with significant variations occurring on a timescale of several seconds to several minutes. Baseline fluctuations can exceed the magnitude of the absorbance signal. It is possible to switch the laser wavelength periodically between the signal peak and a baseline region far from the absorption line in order to measure the baseline, but this scheme is not practical when line-locking is also required. Most experimental protocols for using wavelength modulation spectroscopy, or similar techniques, to quantify weak absorbances include means to scan the nominal, i.e., unmodulated, laser wavelength over a wavelength range that is substantially larger than the absorbance linewidth. The full contour of the harmonic waveform is recorded, permitting determination of the baseline value as well as the amplitudes of the extrema. Instrumentation, such as transient waveform averagers, needed to acquire the full spectral waveform on a timescale that is unperturbed by baseline fluctuations is expensive. Also, the overall measurement response time is reduced because the laser wavelength is not coincident with the absorption line during a significant portion of each measurement period.

Frequency modulation (FM) spectroscopy, described by G. C. Bjorklund (U.S. Pat. No. 4,297,035) is similar to wavelength modulation spectroscopy except that the FM method stipulates modulating the laser at frequency that is comparable to, or larger than, the linewidth of the absorption feature. This modulation produces discrete sidebands symmetrically distributed about the nominal laser frequency and differs from the modulation conditions used for wavelength modulation spectroscopy which generate a continuum of sidebands. In FM spectroscopy, demodulation at the modulation frequency (or higher harmonics) is possible, resulting in spectral lineshapes similar to those shown in FIG. 1. In practice, though, detection at higher harmonics is rarely used with FM spectroscopy due to detector bandwidth limitations.

Frequency modulation spectroscopy is not practical when the optimum modulation frequency exceeds the bandwidth of available detectors. An improvement to FM spectroscopy, two-tone FM spectroscopy, provides some of the advantages of FM spectroscopy while allowing the use of commercially available photodetectors and pre-amplifiers. The two-tone method is described by U.S. Pat. Nos. 4,594,511 and 4,765,736 and by D. E. Cooper and T. F. Gallagher, *Applied Optics* 24, 1327–1334 (1985). Modulation at two frequencies generates groups of sidebands. Sample absorbance is measured by demodulating the detector output at a frequency corresponding to a difference frequency between pairs of sidebands occurring within one of said groups. The most commonly used embodiment of two-tone FM spectroscopy generates spectral waveforms that are similar in shape and symmetry to a 2f waveform, as in trace 14 of FIG. 1(*c*). Two-tone FM spectroscopy differs from the present invention in that the two-tone FM method requires laser modulation at two frequencies and uses one demodulation step in order to obtain a signal proportional to sample absorbance whereas in the present invention only one modulation frequency is required to make an absorbance measurement that is equivalent in information content to the measurement made using two-tone FM spectroscopy. None of the published descriptions of two-tone FM spectroscopy include provisions for laser wavelength stabilization. The advantages and benefits of the present invention can be applied to the two-tone FM technique through the addition of a third modulation frequency and a second demodulation step.

Wavelength modulation spectroscopy including the use of two modulation frequencies has been described by Cassidy and Reid (D. T. Cassidy and J. Reid, *Applied Physics* B 29, 279–285 (1982)). The second modulation frequency provides a method for reducing signals from optical interference fringes. The variations in laser wavelength caused by the second modulation "smears out" the fringes, so that the unwanted signals average to zero. The Cassidy and Reid work differs from the present invention in that only one demodulation is performed; the absorbance signals are susceptible to the sources of baseline noise described above. Cassidy and Reid obtain their optimum result, i.e., the largest ratio of absorbance signal to interference fringe signal, when the higher modulation frequency is an integral multiple of the lower frequency. The present invention would perform poorly given this relationship of modulation frequencies. Also, Cassidy and Reid make no reference to laser wavelength stabilization.

SUMMARY OF THE INVENTION

Disclosure of the Invention

The present invention relates to a method and apparatus for dual modulation of an optical spectroscopy laser. The invention provides wavelength stabilization and improved precision and accuracy of optical absorbance measurements. The invention comprises producing a light beam with a light source; modulating a wavelength of said light source beam with a first and a second frequency (the first frequency being different or greater than the second frequency); and producing output signal(s) representative of a gas species quantity and useful for wavelength stabilization with a detector. The invention also provides for demodulating the detector output signal.

In the preferred embodiment, the light source is a laser, such as a diode laser. The light beam is split into a first portion and a second portion.

The detector comprises a reference detector which produces an output signal representative of a known quantity of the gas species and a sample detector which produces an output signal representative of an unknown quantity of the gas species. The detector may be a is single detector or several detectors which produce signals representative of known and unknown quantities of the gas species and for wavelength stabilization. The detector may also provide demodulation.

The preferred demodulator comprises a first demodulator for demodulating the reference detector output signal and a second demodulator for demodulating the sample detector output signal. Each demodulator may utilize a reference frequency and generate other frequencies, preferably harmonics of the reference frequency. The first demodulating frequency of the first and second demodulators may be greater than the second demodulating frequency of the first and second demodulators; the second demodulating frequency of the first demodulator may be equal to the second demodulating frequency of the second demodulator; or the first demodulating frequency of the second demodulator may be an integral multiple of the first demodulating frequency of the first demodulator. The first demodulator produces a discriminant signal to stabilize the wavelength of the light source. The second demodulator reduces baseline noise in a signal proportional to sample absorbance of the unknown quantity of the gas.

A primary object of the invention is to reduce baseline noise in the signal proportional to sample absorbance.

Still another object of the invention is to provide a discriminant for regulating laser wavelength.

One advantage of the present invention is continuous monitoring of the number density of a gaseous species.

Another advantage of the present invention is its provision of a relatively inexpensive method for quantifying weak optical absorbances with rapid time response.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIG. 2(*a*) illustrates an alternative embodiment of the apparatus of the invention;

FIGS. 3(*a*)–3(*d*) show the spectral waveforms due to demodulation at the major modulation frequency $\Omega$ and the minor modulation frequency $\omega$;

FIGS. 5(*a*)–5(*d*) present experimental data demonstrating the usefulness of the present invention;

DETAILED DESCRIPTION OF THE PREFERRED EMBODIMENTS

Best Modes for Carrying Out the Invention

In accordance with the invention there is provided a method and apparatus for continuous monitoring of a selected gaseous species using a laser-based optical absorbance measurement. The invention is of a novel dual modulation scheme for laser wavelength stabilization that also nulls low frequency baseline noise in the measured sample absorbance. Two simultaneous laser modulation frequencies and up to four demodulation steps are used to generate a signal proportional to absorbance in the sample and a discriminant used to regulate the laser wavelength.

Figure 1A:
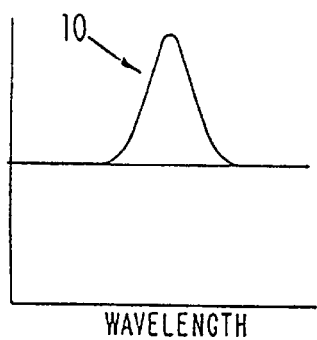
FIG. 1(*a*)–1(*e*) show a representation of an absorbance spectral waveform and the corresponding 1f, 2f, 3f and 4f spectral waveforms respectively.
Figure 1B:
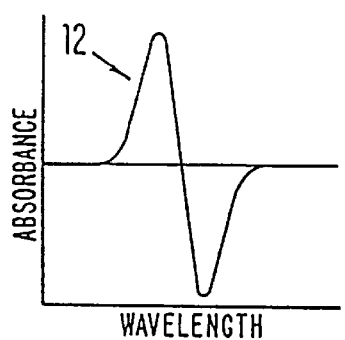
Figure 1C:
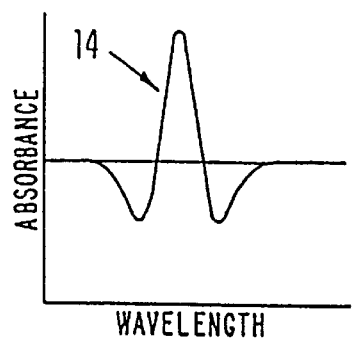
Figure 1D:
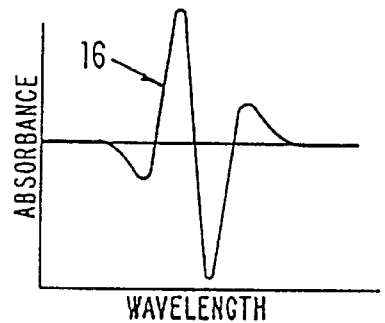

FIG. 1(a) depicts a representative absorption line spectrum 10 of absorbance plotted against wavelength. FIGS. 1(b), 1(c), 1(d), and 1(e) present spectral waveforms of frequencies, 1f, 2f, 3f and 4f corresponding to 12, 14, 16, and 18, respectively.

Figure 2:
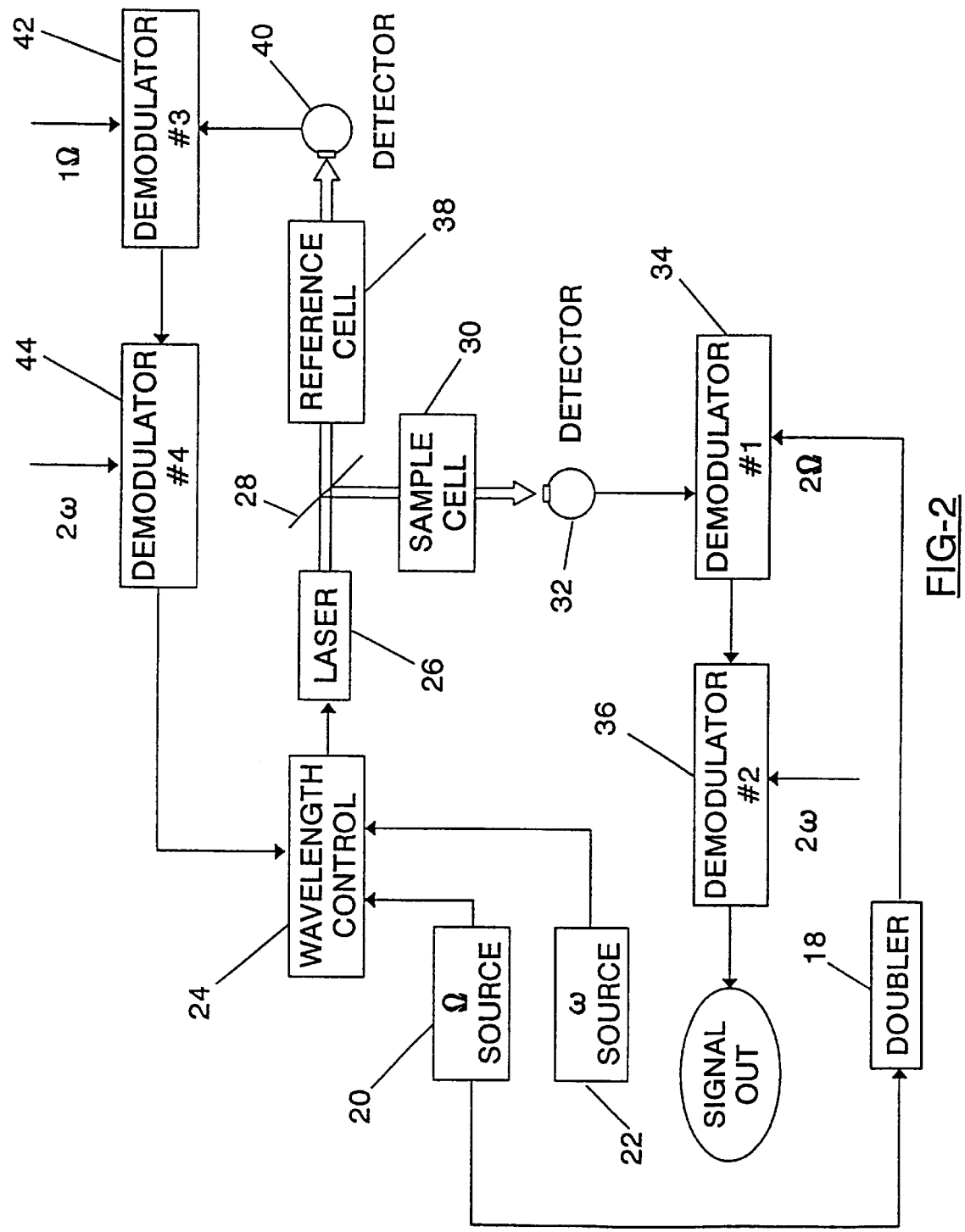
FIG. 2 illustrates the preferred embodiment of the apparatus of the invention.

Reference is now made to the schematic diagram of FIG. 2 depicting the preferred embodiment of the invention. The laser output wavelength is modulated simultaneously using two modulation frequencies, $\Omega$ and $\omega$, with $\Omega >> \omega$ from sources 20 and 22, respectively. A beam splitter or similar device diverts a portion of the laser beam through a region containing a reference quantity of a specified gas and then onto a detector which is known as the reference detector. Another portion of the laser beam is directed through a region containing an unknown quantity of said specified gas, then onto a detector which is known as the sample detector. A line-locking discriminant is obtained by demodulating the reference detector output with respect to an odd harmonic of frequency $\Omega$ followed by demodulation using an even harmonic of frequency $\omega$. The sample absorbance can be quantified and baseline noise nulled by demodulating at an even harmonic of frequency $\Omega$ followed by demodulating the sample detector output at an even harmonic of frequency $\omega$, or by demodulating the sample detector output at an odd harmonic of frequency $\Omega$ followed by an odd harmonic of frequency $\omega$.

Demodulating the reference detector output using an odd harmonic of frequency $\Omega$ followed by demodulation using an even harmonic of frequency $\omega$ produces a spectral waveform exhibiting a zero crossing at the center of the species absorption line. Similarly, demodulating the sample detector output at an even harmonic of frequency $\Omega$ followed by an even harmonic of frequency $\omega$, or by demodulating the detector output at an odd harmonic of frequency $\Omega$ followed by demodulating at an odd harmonic of $\omega$, produces a spectral waveform with an extremum at line center.

Baseline noise reduction is best visualized by considering an example with representative spectral waveforms shown in FIGS. 3(a)–3(d). The demodulation steps are labelled as $nf_i$ where n identifies the frequency harmonic used with i identifying the reference frequency as $\omega$ or $\Omega$. The sample detector output is first demodulated at twice $\Omega$ to produce a $2f_{1\Omega}$ signal 60, FIG. 3(a). The amplitude of the modulation frequency $\omega$ is chosen such that the induced, periodic wavelength excursions are delimited by the minima 62 and 64 of the $2f_\Omega$ lineshape. The $2f_\Omega$ signal is demodulated at twice $\omega$ to produce a spectral waveform 66, FIG. 3(b), which is similar in appearance to a 4f spectral waveform 18. The technique nulls baseline noise because during every modulation period at frequency $\omega$, the $2f_\Omega$ peak and the $2f_\Omega$ troughs are each sampled twice at evenly spaced intervals. Demodulation at $2\omega$ yields a signal proportional to the peak-to-trough difference independent of low frequency baseline fluctuations.

FIGS. 3(a)–3(d) also show the spectral waveforms generated by steps representative of those used to produce the discriminant for wavelength stabilization. Demodulation of the reference detector output at frequency $\Omega$ yields the 1f-like spectral waveform 68, FIG. 3(c). A sequential demodulation at frequency $2\omega$ of the signal yields a spectral waveform 70, FIG. 3(d), similar in appearance to a 3f spectral waveform 16, which is the discriminant for laser wavelength stabilization.

Those skilled in the art will also recognize that the demodulation steps described above can be performed using readily available electronic components, such as double balanced mixers, phase sensitive detectors or lock-in amplifiers. The only restrictions on these demodulation components is that the first demodulation step provide adequate bandwidth so as to transmit with minimal attenuation the electronic frequencies required for the second demodulation step.

The present invention can be implemented using a single optical path and a single detector when the amount of target gas in the sample region is always sufficiently large that the sample can also serve as the reference gas. One such example might be measurements of water vapor in the atmosphere which, for a suitable choice of laser wavelength, guarantees useful absorbance over the full range of anticipated air temperatures and relative humidities. In this case, the electronic output of the detector is divided into two portions; one portion is processed as described previously for a reference detector, the other portion processed as described previously for a sample detector.

Standard line locking practices, in which the reference detector output is demodulated at the modulation frequency, can introduce a significant wavelength offset if the laser power shows a systematic, reproducible variation with changing wavelength. Implementation of the present invention avoids this type of wavelength offset because the wavelength stabilization discriminant is obtained using a spectral waveform similar to a third, or higher odd, derivative-like spectral waveform.

Those skilled in the art will understand that the similarities between frequency modulation spectroscopy and wavelength modulation spectroscopy permit the use of frequency modulation spectroscopy at frequency $\Omega$ instead of wavelength modulation spectroscopy at frequency $\Omega$ in the present invention.

FIG. 2 shows the preferred embodiment of the invention. This embodiment uses a tunable diode laser, such as a Fujitsu model TDL-1270-N-OSI lead-salt diode laser. Diode lasers are well suited to optical analytical methods for detecting trace gaseous species because diode lasers typically produce highly monochromatic radiation and the laser wavelength can be controlled conveniently by changing the laser operating current. Wavelength modulation is effected through AC components of the laser operating current in wavelength control 24, and the wavelength control discriminant is applied as a correction to the DC portion of the laser current.

Laser 26 is mounted within a temperature controlled housing (not shown). The DC portion of the laser current is supplied by a laser current source such as a Spectra Physics diode laser power supply. The laser beam is split by beam splitter 28 into two parts with one part passing through a reference cell 38 before reaching the reference detector 40 while the other portion of the laser beam passes through the sample cell 30 before reaching the sample detector 32. The reference cell 38 is filled with a reference gas such as nitrous oxide, $N_2O$, to a pressure such that an absorbance of approximately 0.5 is measured at an $N_2O$ absorption line that lies within the wavelength tuning range of the diode laser. The reference detector 40, such as a HgCdTe detector shows high quantum yield at the laser wavelength and is equipped with a matched pre-amplifier having sufficient bandwidth to amplify faithfully all detector current AC components at frequencies between $\Omega-2\omega$ and $\Omega+2\omega$. The remainder of the laser beam passes through a sample cell 30 having a total optical path chosen such that the smallest anticipated $N_2O$ number density within the sample will give rise to an absorbance in excess of the minimum detectable absorbance. After exiting the sample cell 30, the laser beam is imaged onto the sample detector 32 which is similar in specification to the reference path detector except that the detector pre-amplifier bandwidth encompasses $2\Omega-2\omega$ to $2\Omega+2\omega$.

The laser modulation waveform contains a sinusoidal portion at frequency $\Omega$ from source 20, equal to 5 MHz, and is obtained from a crystal controlled oscillator such as is sold by Vectron Laboratories, Inc. A portion of the 5 MHz output is combined with the laser current using a simple capacitor circuit. Another portion of the 5 MHz output is used as the local oscillator to provide the 1f demodulation source 42 of the reference detector output. The remainder of the 5 MHz output is frequency doubled, using a doubler 18 such as a Mini-Circuits Model GK-3 to produce a 10 MHz sinusoidal waveform that serves as the local oscillator source 34 for $2f_\Omega$ demodulation of the sample detector 32 output.

The lower frequency portion of the laser modulation waveform is a triangular waveform from source 22 at frequency $\omega$ equal to 1000 Hz and is supplied by the internal modulation circuitry available from the Spectra Physics supply. The signal produced by the $2f_\Omega$ demodulation at source 34 of the sample detector 32 output is connected to the input of a phase sensitive detector 36, such as a Stanford Research Systems Model SRS510 lock-in amplifier. The synchronous square wave output at frequency $\omega$ from the laser power supply provides the reference input to the phase sensitive detector 36 which is configured for second harmonic operation. The signal from the phase sensitive detector 36 is a $2f_\omega$ signal which is proportional to the absorbance by the gas in the sample path.

The signal produced by the $1f_\Omega$ demodulation source at 42 of the reference detector output is connected to the input of a second phase sensitive detector 44. The synchronous square wave output at frequency $\omega$ from the laser power supply provides the reference input to the phase sensitive detector 44 which is configured for second harmonic operation. The signal from the phase sensitive detector 44 is a $2f_\omega$ signal which is connected to the current control input of the laser power supply. The gain and bandwidth settings of the phase sensitive detector are adjusted so as to optimize the frequency stability of the laser where the frequency stability is ascertained indirectly by minimizing the noise on the sample absorbance signal.

Figure 2A:
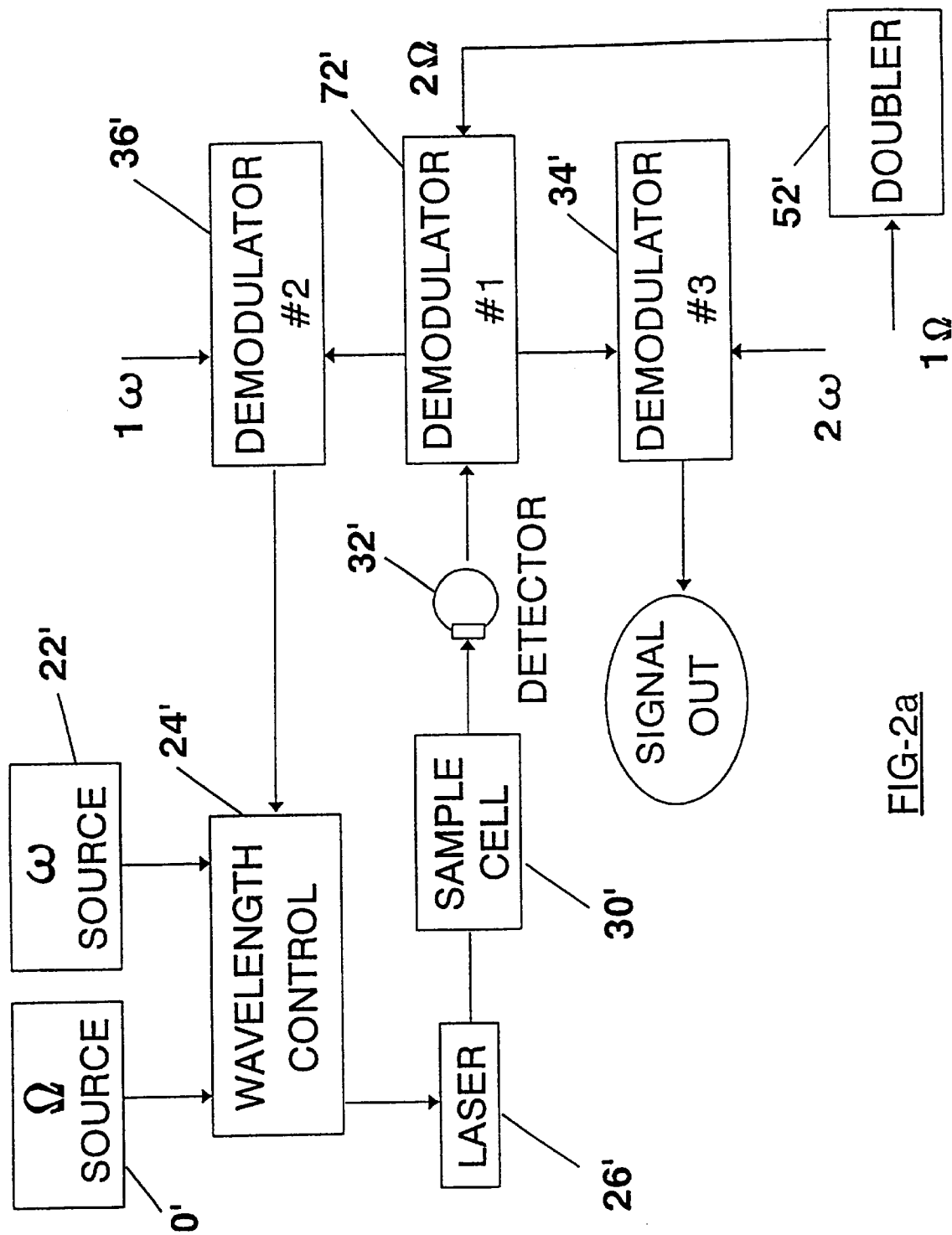

A second embodiment, shown in FIG. 2(a), wherein similar components are primed, uses a single optical path and single detector 32' to provide both the line locking discriminant and a measure of the sample absorbance. In this embodiment, the detector output is demodulated at $2\Omega$ in demodulator 72' and the resulting $2f_\Omega$ signal is split between two subsequent demodulators 34' and 36'. Demodulation synchronous with modulation frequency $\omega$, produces a $1f_\omega$ signal which is used as the line locking signal. Demodulation at $2\omega$ produces a signal that is linearly proportional to the sample absorbance. This second embodiment offers the advantage of requiring only three demodulation steps.

EXAMPLES (INDUSTRIAL APPLICABILITY)

The invention is further illustrated by the following non-limiting examples.

Example 1

Figure 4:
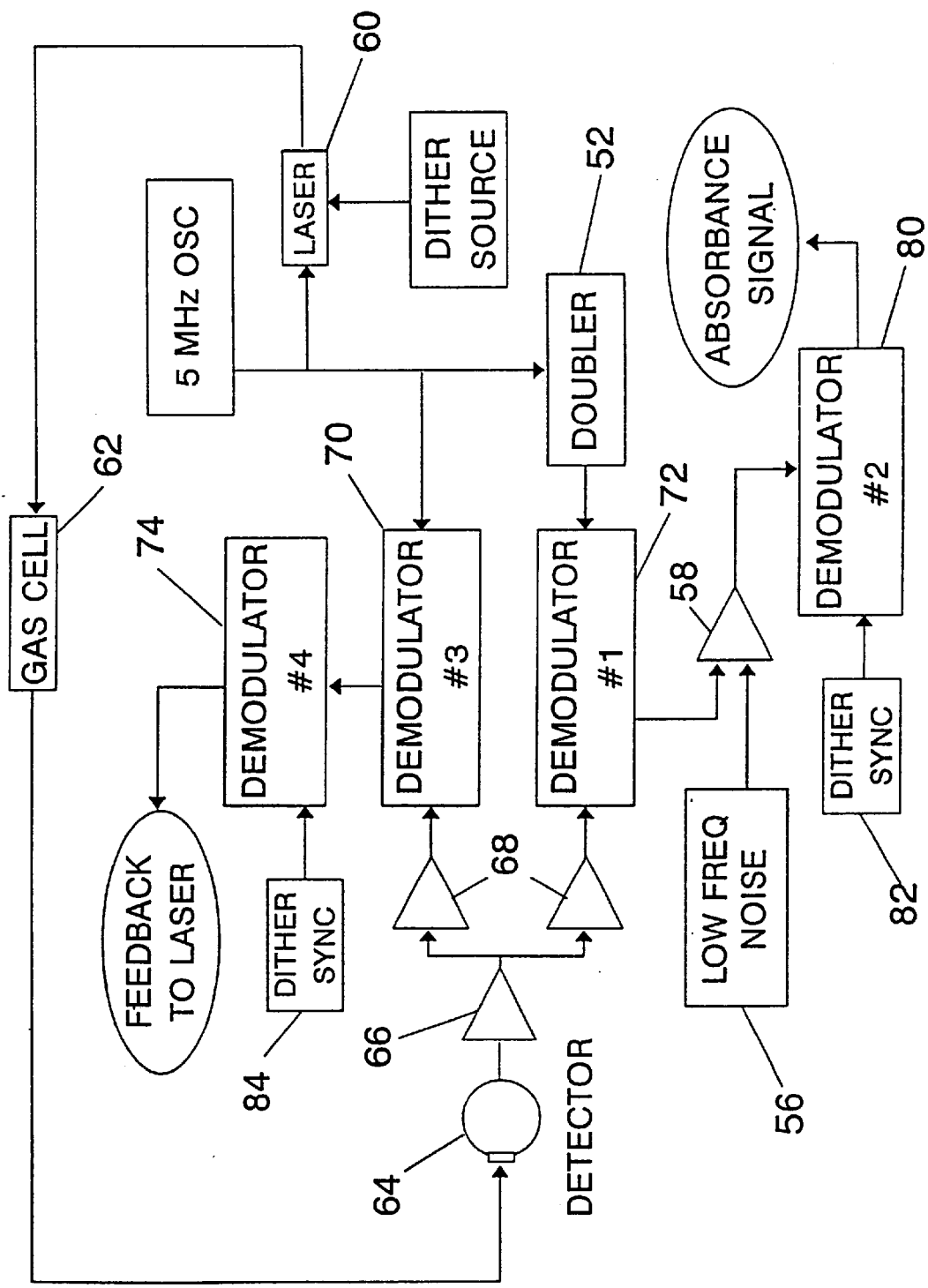
FIG. 4 illustrates a third embodiment of the apparatus of the invention.

FIG. 4. illustrates a third embodiment of the invention, also using a single optical path and a single detector. One gas cell 62 serves as both the sample and reference. The detector and signal processing electronics are shown in FIG. 4. 5 MHz oscillator 110 provides modulation frequency $\Omega$ and Dither Source 112 provides the lower frequency $\omega$ modulation. The output of detector 64 and preamplifier 66 is evenly divided using a 50-50 splitter 68. One portion of the detector output is processed as the reference signal described above with reference to FIG. 2. The other portion is processed as the sample signal, also described above. This third embodiment also includes a sine wave generator 56, operating at 0.013 Hz, that is used to simulate low frequency baseline noise. Output from sine wave generator 56 is combined with the $2f_\Omega$ sample signal using a differential amplifier 58. Dither signals 82 and 84, corresponding to $\omega$ in the FIG. 2 embodiment, are provided. Demodulators 70 and 72 correspond to demodulation sources 42 and 34, respectively. As discussed relative to the FIG. 4 embodiment, double 52 doubles the 5 MHz oscillator output and provides a 10 MHz frequency to demodulation source 72. Demodulator 80 corresponds to demodulator 36 of FIG. 2, while demodulator 74 corresponds to demodulator 44 of FIG. 2.

FIGS. 5(a)–5(d) show measurements made using this third embodiment. The present invention is compared with the conventional approach using the $1f_\Omega$ signal for feedback stabilization. Trace 100 in FIG. 5(a) shows that the conventional line-locking method works well in the absence of low frequency baseline noise: the $2f_\Omega$ signal exhibits less than 0.5% rms fluctuation in a 1 Hz bandwidth. This long term amplitude stability corresponds to better than 0.1 ppm frequency stability. When the feedback control is removed, the $2f_\Omega$ signal drops by half within 1–2 minutes. Baseline fluctuations are demonstrated in FIG. 5(b) by adding a 0.013 Hz sine wave to the $2f_\Omega$ signal, and when baseline fluctuations are included at an amplitude equal to twice the $2f_\Omega$ signal, the fluctuations propagate unattenuated, 102. The fluctuations are removed using the present dual modulation line-locking invention, 104 depicted in FIG. 5(c). The observed $2f_\omega$ signal shows only a small increase in rms noise, from 0.33% to 0.39%, trace 106, FIG. 5(d), to 104, with the addition of low frequency baseline "drift" at twice the $2f_\Omega$ signal amplitude. Baseline fluctuations are attenuated by a factor of 3000.

Example 2

The second signal processing step of the sample detector output can be performed by measuring the magnitude of the power within a narrow bandwidth. The bandwidth includes an even harmonic of $\omega$ if the first sample demodulation was performed using an even harmonic of frequency $\Omega$, or an odd harmonic of frequency $\omega$ if the first sample demodulation was performed using an odd harmonic of frequency $\Omega$. This incoherent signal processing step offers the advantage of eliminating the need for one local oscillator and one phase shifter. Power measuring circuits are commercially available in the form of inexpensive integrated circuits requiring only a bandpass filter to select the desired frequency range and an integrating capacitor used to select the measurement period. An alternative method for measuring the magnitude of the power within a selected bandwidth is to apply the signal simultaneously to two lock-in amplifiers (also known as phase sensitive detectors), each of the amplifiers referenced to the same demodulation frequency but adjusted to be 90° different in phase. The output of the lock-in amplifiers are summed in quadrature to produce a signal indicative of the magnitude of the power within a narrow bandwidth around the demodulation frequency.

Example 3

Figure 6:
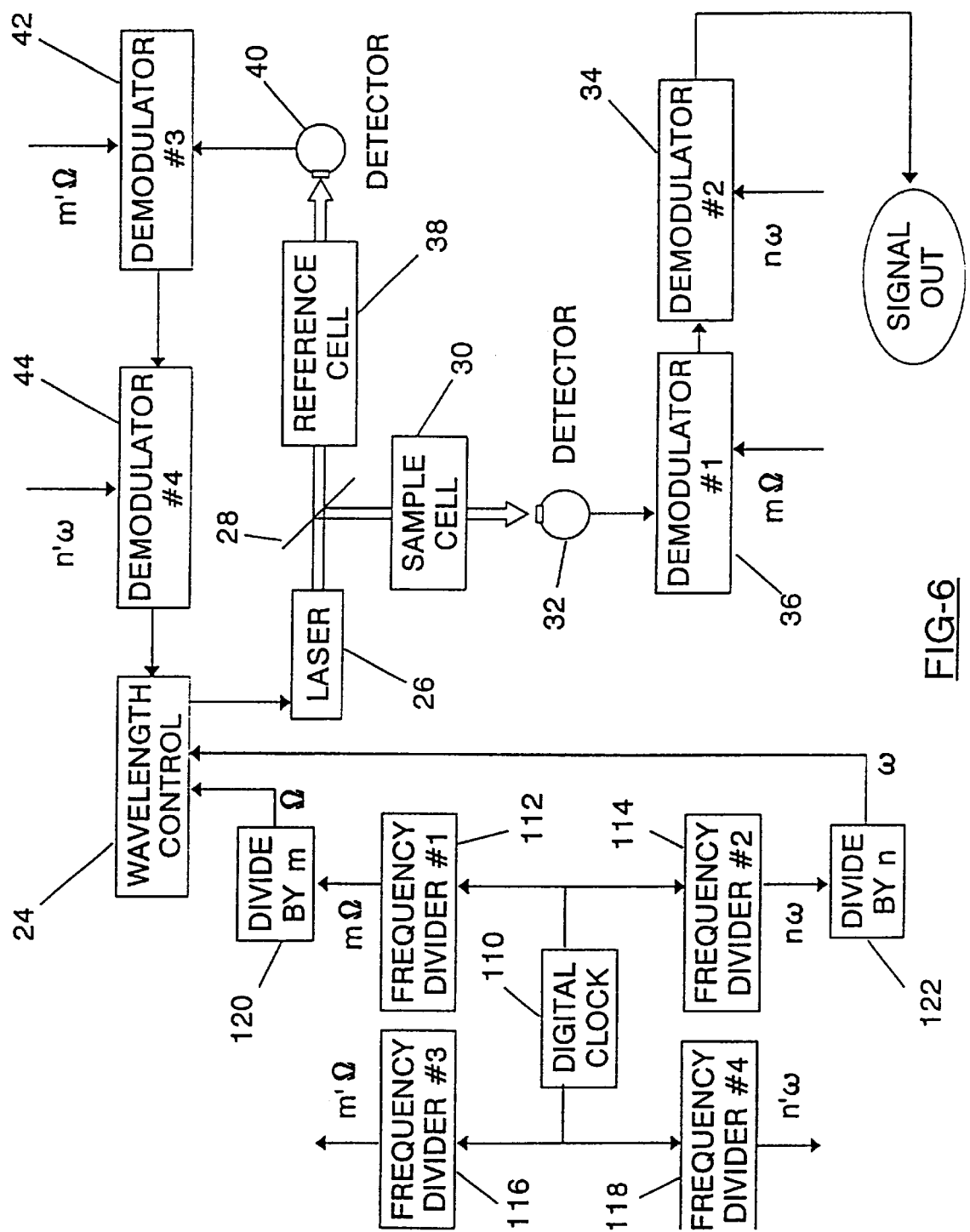
FIG. 6 is an alternative embodiment of the invention.

FIG. 6, illustrates another embodiment of the invention. Modulation frequencies $\Omega$ and $\omega$, as well as demodulation frequencies m$\Omega$, m'$\Omega$, n$\omega$ and n'$\omega$ may all be generated conveniently from a single master digital clock using one commercially available output oscillator 110 and simple digital counting circuit components which function as frequency dividers π1 112, #2 114, #3 116, and #4 118 used to produce frequencies m$\Omega$, n$\omega$ m'$\Omega$, and n'$\omega$, respectively. The master clock frequency, C, is chosen to satisfy the relationships m'$\Omega$=C/$\alpha$', m$\Omega$=C/$\alpha$, n'$\omega$=C/$\beta$' and n$\omega$=C/$\beta$ where $\alpha$', $\alpha$, $\beta$', and $\beta$ are integers [for all required values of m and n]. The modulation frequencies $\Omega$ and $\omega$ are derived from the harmonics m$\Omega$ and n$\omega$, using frequency dividers 120 and 122, respectively. For example, if C=6 Mhz which derives $\Omega$=1 Mhz and m'=3, $\alpha$'=2, m=2 and $\alpha$=3 one also obtains $\omega$=10 Khz with n'=n=2 and $\beta$'=$\beta$=300. The signal from the sample detector 32 is processed using two demodulators in series, 36 and 34, to produce a signal representative of the absorbance within the sample cell 30 that is free from baseline fluctuations. Similarly, the signal from the reference detector 40 is processed using two demodulators in series, 42 and 44, to produce a feedback signal used for laser wavelength stabilization. The choice of integers m', m, n', and n is made so as to obtain a good signal-to-noise ratio for the absorbance measurement and to provide the appropriate symmetries for the output signal from demodulator 34 and for the wavelength stabilization signal from demodulator 44. Specifically, signal-to-noise ratio considerations for the absorbance measurement mean that the frequency m$\Omega$ is large enough to avoid most of the 1/f noise inherent from the laser. The symmetry constraints for processing the signal from the sample detector 32 are that m and n both be odd or both be even. Processing the signal from the reference detector 40 requires that either m' is odd and n' is even or that m' is even and n' is odd. These symmetries result in an absorbance measurement output signal from demodulator 34 that has an extremum at the absorbance line center and a wavelength stabilization signal from demodulator 44 that exhibits a zero crossing at line center. The phases of the digital waveforms are easily controlled using simple, inexpensive digital timing circuit components such as monostables, digital counters or delay generators. Bandpass filtering of said digital waveforms provides sinusoidal waveforms suitable for modulation and demodulation.

Example 4

Figure 7:
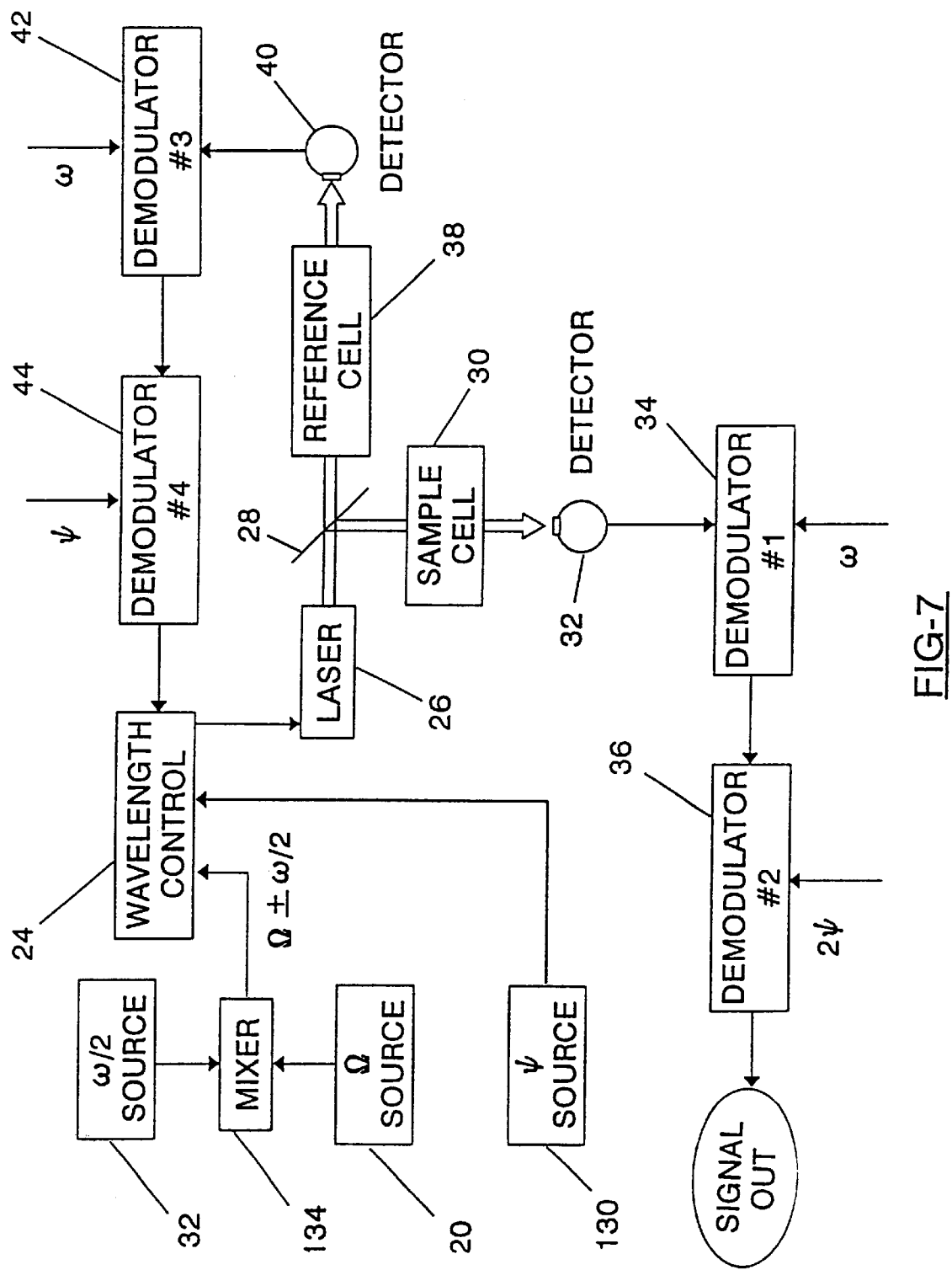
FIG. 7 is yet another alternative embodiment of the invention.

The present invention can also be implemented as an improvement to two-tone FM spectroscopy. In the most commonly used embodiment of two-tone FM spectroscopy, the laser is modulated at frequencies $\Omega$+$\omega$/2 and $\Omega$-$\omega$/2 (with $\Omega$<<$\omega$) and the sample absorbance is measured by demodulating the detector output signal at frequency $\omega$. The resulting two-tone FM spectral lineshape is shown in FIGS. 3 and 4 of U.S. Pat. No. 4,765,736 and is similar in shape and symmetry to a 2f waveform 14 of FIG. 1(c). In the present invention, shown in FIG. 7, modulation frequencies $\Omega$+$\omega$/2 and $\Omega$-$\omega$/2 are generated by mixing the output of $\Omega$ source 20 with the output of $\omega$/2 source 132 using mixer 134. Simultaneous application of a third modulation frequency, $\psi$, from source 130 with optimum amplitude chosen such that the induced, periodic wavelength excursions are delimited by the minima of the two-tone FM lineshape allows for sequential demodulations, similar to those described above using demodulators #1 34, #2 36, #3 42, and #4 44, in which demodulation of a two-tone FM signal at an even harmonic of $\psi$ provides a signal proportional to absorbance and free from baseline fluctuations while demodulation at an odd harmonic of $\psi$ provides a signal suitable for wavelength stabilization.

Example 5

Figure 1E:
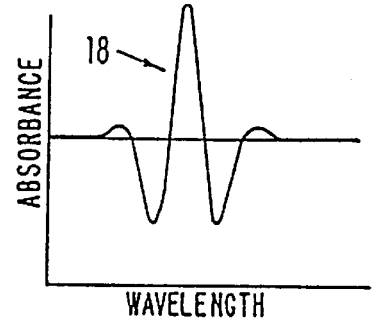

In a further improvement to the embodiment illustrated in FIG. 2, the output of the reference detector 40 is split into two portions which are processed to produce both a discriminant for laser wavelength stabilization and a signal similar to waveform 18 of FIG. 1(e), which is at an extremum when the laser wavelength is adjusted to the center of the absorbance feature. Continuous monitoring of the latter signal provides a secondary method for verifying the performance of the laser spectrometer. The line-locking signal is zero when the laser wavelength is properly adjusted, but can also be zero if the laser wavelength is far from the absorbance wavelength. The combination of a line-locking signal that is near or at zero and an absorbance signal that is far from zero provides a more useful indicator of correct system performance than does the magnitude of the line-locking signal alone.

The preceding examples can be repeated with similar success by substituting the generically or specifically described reactants and/or operating conditions of this invention for those used in the is preceding examples.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosure of all applications, patents, and publications cited above, and of the corresponding application are hereby incorporated by reference.

What is claimed is:

1. Optical spectroscopy apparatus providing wavelength stabilization and improved precision and accuracy of optical absorbance measurements, the apparatus comprising:

light source means for producing a light beam;

modulator means for modulating a wavelength of said light source means, said modulator means comprising means for simultaneously modulating said wavelength with a first frequency and a second frequency, said first frequency being different than said second frequency;

detector means positioned to receive said light beam for producing output signal means comprising signal means for wavelength stabilization of said light source means and signal means representative of an absorber species quantity; and demodulator means for demodulating said output signal means, said demodulator means comprising first and second demodulator means each performing sequential demodulations, wherein a first demodulating frequency of said first and said second demodulator means is greater than a second demodulating frequency of said first and second demodulator means.

2. The invention of claim 1 wherein said light source means comprises laser means.

3. The invention of claim 2 wherein said laser means comprises diode laser means.

4. The invention of claim 1 wherein said light beam is split into a first portion and a second portion.

5. The invention of claim 4 wherein said detector means comprises a first detector for producing said signal means representative of an absorber species quantity and a second detector means for producing said signal means for wavelength stabilization.

6. The invention of claim 1 wherein said modulator means further comprises means for modulating said wavelength with a third frequency, said third frequency being different than said first and second frequencies.

7. The invention of claim 6 wherein said third frequency corresponds to a frequency of said wavelength stabilization means.

8. The invention of claim 1 wherein said modulator means and said demodulator means comprise master digital clock means.

9. The invention of claim 1 wherein a first demodulating frequency of said first demodulator means is equal to a first demodulating frequency of said second demodulator means.

10. The invention of claim 1 wherein a second demodulating frequency of said first demodulator means is equal to a second demodulating frequency of said second demodulator means.

11. The invention of claim 1 wherein a first demodulating frequency of said first demodulator means and a first demodulating frequency of said second demodulator means are integral multiples of a common frequency.

12. The invention of claim 1 wherein said first demodulator means produces from said signal means for wavelength stabilization a discriminant signal to stabilize the wavelength of said light source means.

13. The invention of claim 1 wherein said second demodulator means reduces a baseline noise in said signal means representative of an absorber species quantity.

14. The invention of claim 1 wherein said detector means comprises reference detector means for producing reference signal means representative of a known quantity of the absorber species.

15. The invention of claim 1 wherein said detector means comprises sample detector means for producing sample signal means representative of an unknown quantity of the absorber species.

16. The invention of claim 15 wherein said apparatus further comprises means for measuring a power magnitude of said sample signal means within a narrow bandwidth.

17. The invention of claim 16 wherein said means for measuring a power magnitude of said sample signal means within a narrow bandwidth comprises root-mean-square (rms) power circuit means.

18. The invention of claim 16 wherein said means for measuring a power magnitude of said sample signal means within a narrow bandwidth comprises lock-in amplifier means.

19. The invention of claim 18 wherein said lock-in amplifier means comprises means for providing said sample signal means to two lock-in amplifiers, each said amplifier referenced to a demodulation frequency and adjusted 90 degrees different in phase from each other, and providing output summed in quadrature.

20. The invention of claim 1 wherein said detector means comprises a single detector means for producing output signal means representative of known and unknown quantities of the absorber species.

21. A method for providing wavelength stabilization and improving precision and accuracy of optical absorbance measurements in optical spectroscopy apparatus, the method comprising the steps of:

providing a light source for producing a light beam;

simultaneously modulating a wavelength of the light source with a first frequency and a second frequency, the first frequency being different than the second frequency;

producing by a detector positioned to receive the light beam an output signal for wavelength stabilization of the light source and an output signal representative of an absorber species quantity; and demodulating the detector output signals by a demodulator comprising first and second demodulators each performing sequential demodulations wherein a first demodulating frequency of the first and second demodulators is greater than a second demodulating frequency of the first and second demodulators.

22. The method of claim 21 wherein the step of providing a light source comprises the step of providing a laser.

23. The method of claim 22 wherein the step of providing a laser comprises the step of providing a diode laser.

24. The method of claim 21 wherein the step of producing a light beam further comprises the step of splitting the light beam into a first portion and a second portion.

25. The method of claim 24 wherein the step of producing an output signal representative of an absorber species quantity and an output signal for wavelength stabilization comprises the step of utilizing one detector for producing an output signal representative of an absorber species quantity and another detector for producing an output signal for wavelength stabilization.

26. The method of claim 21 wherein the step of modulating a wavelength of a light source further comprises the step of modulating the wavelength at a third frequency, the third frequency being different than the first and second frequencies.

27. The method of claim 26 wherein the step of producing an output signal providing for wavelength stabilization comprises the step of utilizing the third frequency to provide for wavelength stabilization.

28. The method of claim 21 wherein the steps of modulating the light source wavelength and demodulating the detector output signals comprise the step of providing frequencies for modulation and demodulation from a master digital clock.

29. The method of claim 21 wherein the step of demodulating the detector output by a first and second demodulator comprises the step of providing a first demodulating frequency of the first demodulator equal to a first demodulating frequency of the second demodulator.

30. The method of claim 21 wherein the step of demodulating comprises the step of providing a second demodulating frequency of the first demodulator equal to a second demodulating frequency of the second demodulator.

31. The method of claim 21 wherein the step of demodulating comprises the step of providing a first demodulating frequency of the first demodulator and a first demodulating frequency of the second demodulator, both being integral multiples of a common frequency.

32. The method of claim 21 wherein the step of demodulating comprises the step of producing from the first demodulator and the output signal for wavelength stabilization a discriminant signal used to stabilize the wavelength of the light source.

33. The method of claim 21 wherein the step of demodulating comprises the step of reducing by the second demodulator a baseline noise in the output signal representative of an absorber species quantity.

34. The method of claim 21 wherein the step of producing an output signal representative of an absorber species quantity comprises the step of providing a reference detector producing a reference output signal representative of a known quantity of the absorber species.

35. The method of claim 21 wherein the step of producing an output signal representative of an absorber species quantity comprises the step of providing a sample detector for producing a sample output signal representative of an unknown quantity of the absorber species.

36. The method of claim 35 wherein the step of producing an output signal representative of an absorber species quantity comprises the step of measuring a power magnitude of the sample output signal within a narrow bandwidth.

37. The method of claim 36 wherein the step of measuring a power magnitude of the sample output signal within a narrow bandwidth comprises the step of measuring with a root-mean-square power circuit.

38. The method of claim 36 wherein the step of measuring a power magnitude of the sample output signal within a narrow bandwidth comprises the step of measuring with a lock-in amplifier circuit.

39. The method of claim 38 wherein the step of measuring with a lock-in amplifier circuit comprises the steps of:

a) applying the output signal simultaneously to two lock-in amplifiers;

b) referencing the lock-in amplifiers to a same demodulation frequency;

c) adjusting the lock-in amplifiers to be 90 degrees different in phase; and d) summing the outputs of the lock-in amplifiers in quadrature.

40. The method of claim 21 wherein the step of producing an output signal representative of an absorber species quantity comprises the step of providing a single detector producing signals representative of known and unknown quantities of the absorber species.

* * * * *